US007453977B2

(12) United States Patent
DiBianca et al.

(10) Patent No.: US 7,453,977 B2
(45) Date of Patent: Nov. 18, 2008

(54) VARIABLE RESOLUTION X-RAY CT DETECTOR WITH TARGET IMAGING CAPABILITY

(75) Inventors: Frank A. DiBianca, Memphis, TN (US); Lawrence M. Jordan, Washington, DC (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 11/672,071

(22) Filed: Feb. 7, 2007

(65) Prior Publication Data

US 2007/0181813 A1     Aug. 9, 2007

Related U.S. Application Data

(60) Provisional application No. 60/771,177, filed on Feb. 7, 2006.

(51) Int. Cl.
*G01N 23/00* (2006.01)
(52) U.S. Cl. .............................. 378/19; 378/4; 378/98.8
(58) Field of Classification Search ................. 378/19, 378/98.8, 4–20
See application file for complete search history.

(56) References Cited

U.S. PATENT DOCUMENTS

| | | | |
|---|---|---|---|
| 4,417,354 A | 11/1983 | Pfeiler | |
| 4,429,227 A | 1/1984 | DiBianca et al. | |
| 5,355,309 A * | 10/1994 | Eberhard et al. | 378/15 |
| 6,285,739 B1 | 9/2001 | Rudin et al. | |
| 6,335,957 B1 | 1/2002 | DiBianca | |
| 6,725,078 B2 | 4/2004 | Bucholz et al. | |
| 7,147,372 B2 * | 12/2006 | Nelson et al. | 378/207 |

* cited by examiner

*Primary Examiner*—Jurie Yun
(74) *Attorney, Agent, or Firm*—Luedeka, Neely & Graham, P.C.

(57) ABSTRACT

Variable-Resolution X-ray (VRX) techniques boost spatial resolution of a Computed Tomographic (CT) scanner in the scan plane by two or more orders of magnitude by reducing the angle of incidence of the x-ray beam with respect to the detector surface. A multi-arm multi-angle VRX detector for targeted CT scanning allows for "target imaging" in which an area of interest is scanned at higher resolution than the remainder of the subject, yielding even higher resolution for the target area than that obtained from prior VRX techniques. In one embodiment, the VRX-CT detector comprises four quasi-identical arms, each containing six 24-cell modules made of individual custom CdWO4 scintillators optically-coupled to custom photodiode arrays. The maximum scan field is 40 cm for a magnification of 1.4. A significant advantage of the four-arm geometry is that it can transform quickly to a two-arm or single-arm geometry for comparison studies and other applications.

19 Claims, 10 Drawing Sheets

VARIABLE RESOLUTION X-RAY CT DETECTOR WITH TARGET IMAGING CAPABILITY

This application claims priority to provisional patent application Ser. No. 60/771,177 filed Feb. 7, 2006, titled VARIABLE RESOLUTION X-RAY CT DETECTOR WITH TARGET IMAGING CAPABILITY.

The present invention was developed at least in part with funding received from the National Institutes of Health grant number EB-00418. The U.S. government may have certain rights in this invention.

FIELD

This invention relates to the field of Computed Tomographic (CT) x-ray scanners. More particularly, this invention relates to a Targeting Variable Resolution (TVRX) CT x-ray scanner. According to the invention, the spatial resolution over a portion of a target zone can be greatly increased by reducing the projected size of CT detector elements in a detector array, such as by angulating a portion of the detector array or by using a stair-case detector array design.

BACKGROUND

Computed Tomographic x-ray scanners (referred to herein as "CT scanners") have been in clinical use since the early 1970s. Generally, a CT scanner uses a rotating x-ray beam and detector to make cross-sectional (or three-dimensional) images of human anatomy and other subjects. A major disadvantage of current CT scanners is the inability to substantially increase the spatial resolution when the size of the subject under examination decreases. Moreover, the spatial resolution of prior CT scanners cannot be substantially increased when one wishes to target a specific area of anatomy for detailed examination.

Prior variable resolution (VRX) techniques have boosted spatial resolution of CT detectors in the scan plane by two or more orders of magnitude. Generally, this has been accomplished by decreasing the angle of incidence of the x-ray beam relative to the surface of the detector array, thereby reducing the projected detector spacing. In prior single-arm angled detector geometries, there have been problems with non-symmetry from one side to the other side of the detector array. Also, in prior systems, the total variation in the sampling aperture has been relatively large and the maximum local system magnification has been large, which reduced overall system resolution unless extremely small focal spots were employed. Dual-arm detectors have offered an improvement over single-arm detectors by providing left-right symmetry, reduction in the total variation in the line-spread function (LSF), and reduction of the maximum system magnification. However, prior dual-arm detectors have had a gap or discontinuity at the central detector cells where the two arms meet, and there have been problems with inter-arm x-ray scattering.

Thus, prior VRX-CT scanners have provided increased spatial resolution by reducing the detector angle to reduce its projected size and the corresponding size of the scan circle. However, if the scan circle was reduced too much, the object being imaged no longer fit inside the scan circle. To reduce the scan circle even smaller would produce reconstruction artifacts created by structures outside the scan circle which are not sampled in all views (projections).

What is needed, therefore, is a VRX-CT x-ray scanner having an improved geometry that provides increased spatial resolution without the problems associated with prior single-arm and dual-arm scanner designs.

SUMMARY

One embodiment of the present invention provides a four-arm VRX-CT scanner which overcomes the problems of prior multi-arm scanner designs. The two inner arms of the four-arm detector continue to reduce in angle over a progressively-smaller target scan circle exhibiting progressively-higher spatial resolution, while the two outer arms increase in angle so as to span the minimum acceptable scan circle. In this manner, the scanner produces a complete set of scan projections that all span the entire object but have increased resolution inside a target circle and lower resolution outside the circle. This yields high-quality reconstructions inside the target circle. Accordingly, the multi-arm geometry of the present invention allows "targeted imaging" with the accompanying extremely-high local spatial resolution.

In one preferred embodiment, the invention provides an apparatus for generating x-ray images of a subject. The apparatus includes an x-ray radiation source for directing x-ray radiation along a radiation axis toward the subject, a detector array for receiving the x-ray radiation as altered by the subject, and means for processing signals generated by the detector array to generate a human-perceivable image of the subject. The detector array of this embodiment comprises a plurality of array arms, where each array arm includes a plurality of detector cells. The detector cells receive and detect the x-ray radiation at a spatial resolution which is dependent at least in part on the number of detector cells in each array arm and the orientation of the array arms with respect to the radiation axis of the x-ray radiation source.

The plurality of array arms include a first array arm and a second array arm. The first array arm is operable to be positioned at a first angle with respect to the radiation axis, such that the first array arm has a first spatial resolution determined at least in part by a value of the first angle. The first array arm includes a first portion of the detector cells for receiving and detecting x-ray radiation that passes through a first zone of the subject. The second array arm is operable to be positioned at a second angle with respect to the radiation axis, such that the second array arm has a second spatial resolution determined at least in part by a value of the second angle which may be different from the value of the first angle. The second array arm includes a second portion of the detector cells for receiving and detecting x-ray radiation that passes through a second zone of the subject.

In a preferred embodiment, the detector array also includes a third array arm and a fourth array arm. The third array arm of this embodiment is operable to be positioned at a third angle with respect to the radiation axis, such that the third array arm has a third spatial resolution determined at least in part by a value of the third angle. The third array arm includes a third portion of the detector cells for receiving and detecting x-ray radiation that passes through the first zone of the subject. The fourth array arm is operable to be positioned at a fourth angle with respect to the radiation axis, such that the fourth array arm has a fourth spatial resolution determined at least in part by a value of the fourth angle which may be different from the value of the third angle. The fourth array arm includes a fourth portion of the detector cells for receiving and detecting x-ray radiation that passes through the second zone of the subject.

In the four-arm embodiment of the detector array, the first and second array arms are preferably disposed to one side of the source radiation axis, and the third and fourth array arms are disposed to an opposite side of the source radiation axis. Also in this embodiment, the first array arm and the third array arm form a vertex of the detector array, which vertex is disposed on or adjacent the radiation axis. In some configurations of the four-arm embodiment, the value of the first angle is substantially equivalent to the value of the third angle, and the value of the second angle is substantially equivalent to the value of the fourth angle, thereby providing array symmetry about the radiation axis.

The targeted VRX-CT imaging provided by the various embodiments of the invention has many areas of application including increasing the resolution of structural details in bodily organs, tumors and other neoplasms, vascular structures, bone structure in the spine, long bones and skull, microcalcifications in breast imaging, intervertebral disks, ligaments, tendons and other connective tissues.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
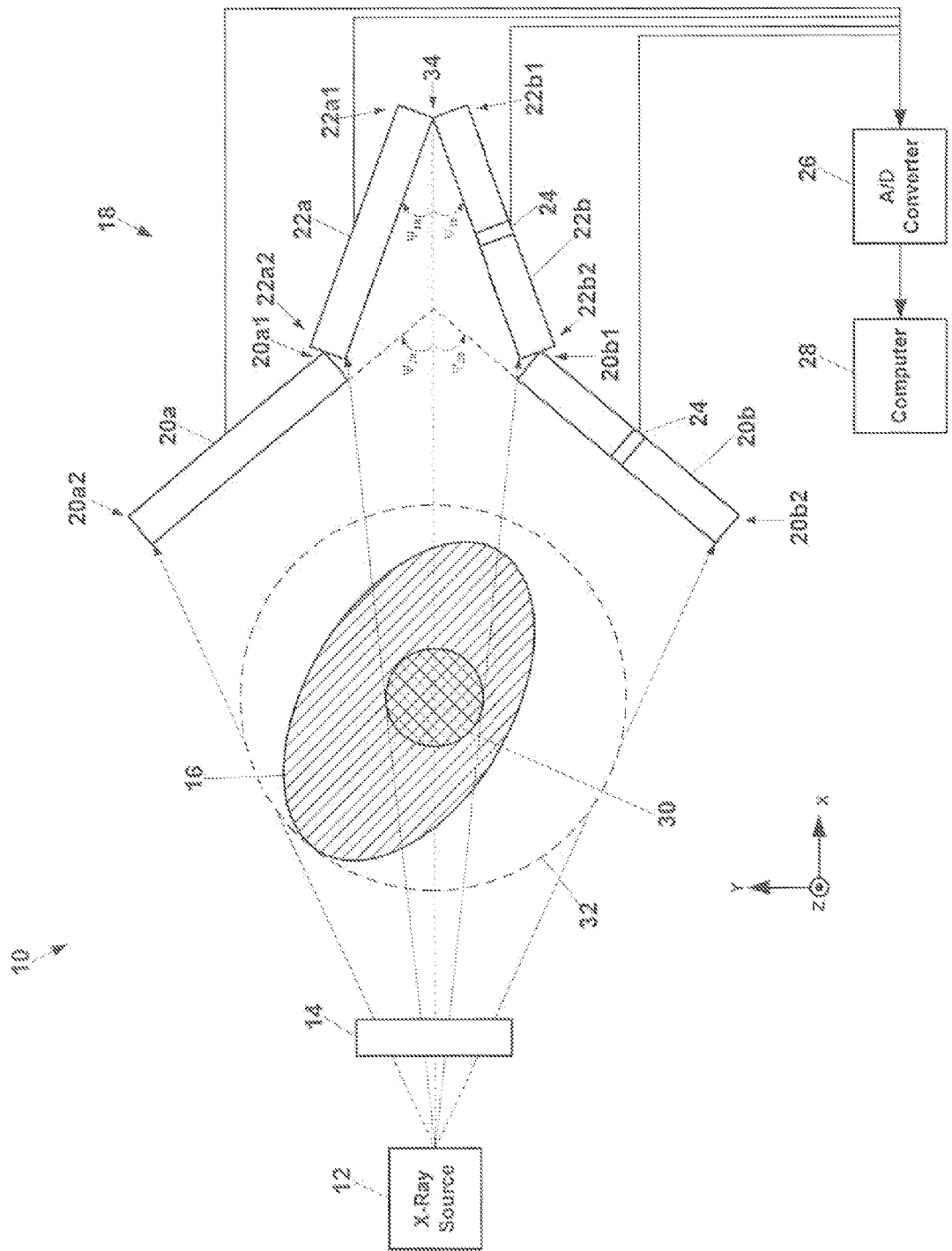
FIG. 1 depicts a four-arm targeting variable-resolution CT x-ray scanner according to a preferred embodiment of the invention.

A preferred embodiment of a four-arm targeting VRX CT scanner system 10 is shown in FIG. 1. In this embodiment, the system 10 includes an x-ray radiation source 12, slice collimator 14, detector array 18, analog-digital converter 26 and computer system 28. X-ray radiation from the x-ray source 12 passes through a subject 16 positioned within a scan field 32 between the source 12 and the detector array 18. As described in more detail below, after the x-ray radiation passes through and is modified by the subject 16, the radiation is received and detected by the detector array 18. The analog-digital converter 26 converts the detected analog signals from the detector array 18 into digital signals that are processed by the computer system 28 to generate images of the subject 16. In one embodiment, a rotating table supports the subject 16 during a scan. In another embodiment, the subject remains stationary and the x-ray source 12, slice collimator 14 and detector array 18 are rotated around the subject 16. In configurations wherein the A/D converter 26 is physically located with the detector array 18, the A/D converter 26 may also rotate around the subject 16 with the array 18.

In a preferred embodiment, the x-ray source 12 comprises a radiographic x-ray tube, such as model number G-1582BI manufactured by Varian Medical Systems, which operates at a nominal anode input power of about 60 kW with a bias voltage of about 60 kV(peak) and generates a focal spot size of about 0.6 mm. In an alternative embodiment, the x-ray source 12 comprises a micro-focus x-ray tube, such as model SB-80-250 manufactured by Source-Ray, Inc., which operates at about 80 kV(peak) and generates a focal spot size of about 36 μm by 65 μm.

The slice collimator 14 confines and directs the x-ray radiation to a specific region or "slice" of the subject 16. In a preferred embodiment, the slice collimator 14 has an adjustment range for slice thickness ranging from about 0-10 mm and is typically set to about 0.5 mm. In some embodiments of the invention, the collimator 14 comprises a multi-slice collimator for directing the x-ray radiation simultaneously to more than one "slice" of the subject 16.

In the embodiment of FIG. 1, the detector array 18 comprises four detector arms, including two outer arms 20a and 20b and two inner arms 22a and 22b. The inner array arms are also referred to herein as a first array arm 22a and a third array arm 22b. The outer array arms are also referred to herein as a second array arm 20a and a fourth array arm 20b. In a preferred embodiment, the inner arms 22a-22b and outer arms 20a-20b are each about 14.4 cm in length, providing a total array length of 55.6 cm (when the arms are aligned end-to-end). As shown in FIG. 1, the first array arm 22a includes a first end 22a1 and a second end 22a2, the second array arm 20a includes a first end 20a1 and a second end 20a2, the third array arm 22b includes a first end 22b1 and a second end 22b2, and the fourth array arm 20b includes a first end 20b1 and a second end 20b2. In preferred embodiments, each array arm 20a-b and 22a-b is operable to pivot about its first end. As shown in FIG. 1, the first end 22a1 of the first array arm 22a is disposed adjacent the first end 22b1 of the third array arm 22b to form a central vertex 34 of the array 18.

In one exemplary embodiment, each detector arm comprises six detector modules. Each of the six detector modules of this embodiment includes twenty-four $CdWO_4$ crystal-photodiode scintillator cells 24. Thus, in this exemplary embodiment, the array 18 includes a total of 576 cells. It will be appreciated that the array 18 could comprise any number of modules and cells. Thus, the invention is not limited to any particular number or arrangement of cells or modules in the detector array 18. So as not to overcomplicate FIG. 1, only two cells 24 are depicted therein. The preferred center-to-center spacing of the scintillator cells 24 is 1 mm. This provides a maximum scan field of about 40 cm with a magnification of 1.4. A typical 360° scan time is about four seconds using a radiographic x-ray tube for the x-ray source 12 and about 20 seconds using a micro-focus tube.

In an alternative embodiment of the invention, the arms 20a-20b and 22a-22b each include a multi-row discrete detector array, or a flat-panel detector array comprising detector cells arranged in a two-dimensional grid. Examples of such multi-row detector arrays include 64-row detectors. Examples of such flat-panel detector arrays include 1000×1000 cell arrays and 2000×2000 cell arrays.

As shown in FIG. 1, the first (inner) arm 22a of the array 18 is positioned at a first angle $\psi_{1a}$ relative to the central radiation axis of the source 12, and the third (inner) arm 22b is positioned at a third angle $\psi_{1b}$ relative to the central radiation axis. In accordance with the invention, the angles $\psi_{1a}$ and $\psi_{1b}$ may be varied from near zero degrees up to 90 degrees, with the selection of angles $\psi_{1a}$ and $\psi_{1b}$ depending on the size of the target zone 30 of the subject 16 and the desired detector resolution within the target zone 30. The second (outer) arm 20a of the array 18 is positioned at a second angle $\psi_{2a}$ relative to the radiation axis of the source 12, and the fourth (outer) arm 20b is positioned at a fourth angle $\psi_{2b}$ relative to the radiation axis. In preferred embodiments of the invention, the angles $\psi_2$ and $\psi_{2b}$ may be varied from the value of the angles $\psi_{1a}$ and $\psi_{1b}$ up to 90 degrees, where the selection of angles $\psi_{2a}$ and $\psi_{2b}$ depend on the overall size of the subject 16 and the desired detector resolution outside the target zone 30. As the angles $\psi_{1a}$ and $\psi_{1b}$ are adjusted to move the second ends 22a2 and 22b2 of the inner arms 22a-22b, the positions of the first ends 20a1 and 20b1 of the outer arms 20a-20b are moved accordingly so that no part of the outer arms 20a-20b blocks the projected "field of view" of the inner arms 22a-22b and also so that there is no gap or discontinuity in the detected signal at the junctions where the outer arms 20a-20b meet the inner arms 22a-22b.

As discussed in more detail hereinafter, the value of the first angle $\psi_{1a}$ between the first arm 22a and the radiation axis may be different from the value of the third angle $\psi_{1b}$ between the third arm 22b and the radiation axis. Also, the value of the second angle $\psi_{2a}$ between the second arm 20a and the source axis may be different from the value of the fourth angle $\psi_{2b}$ between the fourth arm 20b and the source axis. Thus, the number of combinations of positions of the array arms 20a-20b and 22a-22b is literally infinite.

Figure 2:
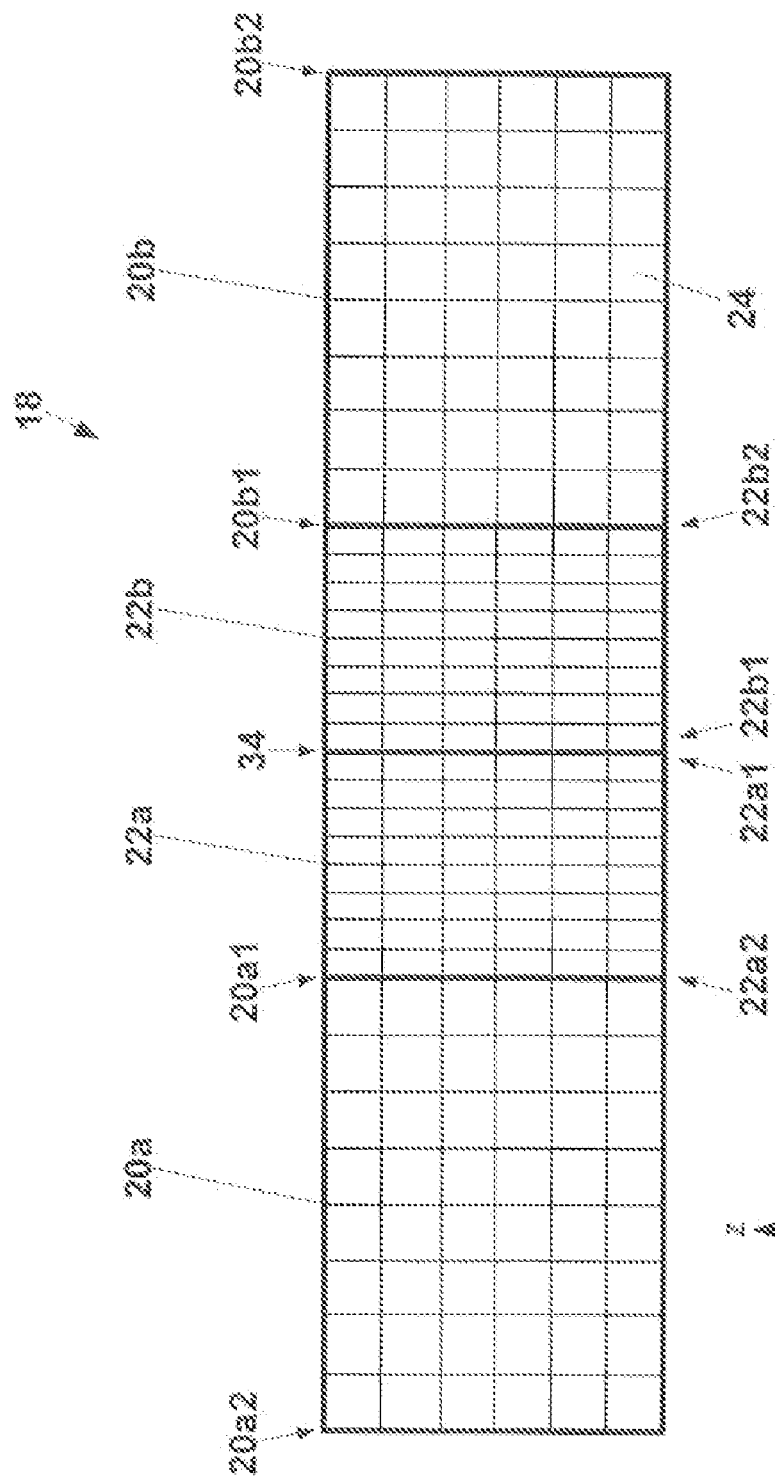
FIG. 2 depicts a front view of the detector array of the four-arm variable-resolution CT x-ray scanner shown in FIG. 1.

FIG. 2 depicts a view in the X-direction of the detector array 18. (See the XYZ coordinate axis indicator in FIG. 1.) This is an example of a view looking toward the array 18 from the position of the source 12. The array 18 depicted in FIG. 2 has fewer cells shown than would be present in the preferred embodiment of the invention so as not to overcomplicate the representation of the array features. This view most clearly indicates that the projected spacing of the cells in the two inner arms 22a-22b is smaller than the projected spacing of the cells in the two outer arms 20a-20b when the arms are angled as shown in FIG. 1. In the configuration depicted in FIG. 2, $\psi_{1a} = \psi_{1b} \approx 30°$ and $\psi_{2a} = \psi_{2b} = 90°$. Generally, for any of the array arms, as the angle $\psi$ between an array arm and the source axis decreases, the spatial image resolution of the array arm increases according to a resolution improvement factor of $1/\sin(\psi)$.

As shown in FIG. 1, the analog/digital (A/D) converter 26 receives analog sample signals from the detector cells 24 and converters the analog sample signals into digital sample signals. The digital sample signals are provided to the computer system 28 for image processing. In a preferred embodiment, the A/D converter 26 is a 16-bit device that samples the detector signals every 2.5 mS. As described in more detail below, the computer system 28 executes software applications to calibrate the system 10 and to process the digital sample signals to generate images of slices of the subject 16.

Figure 3:
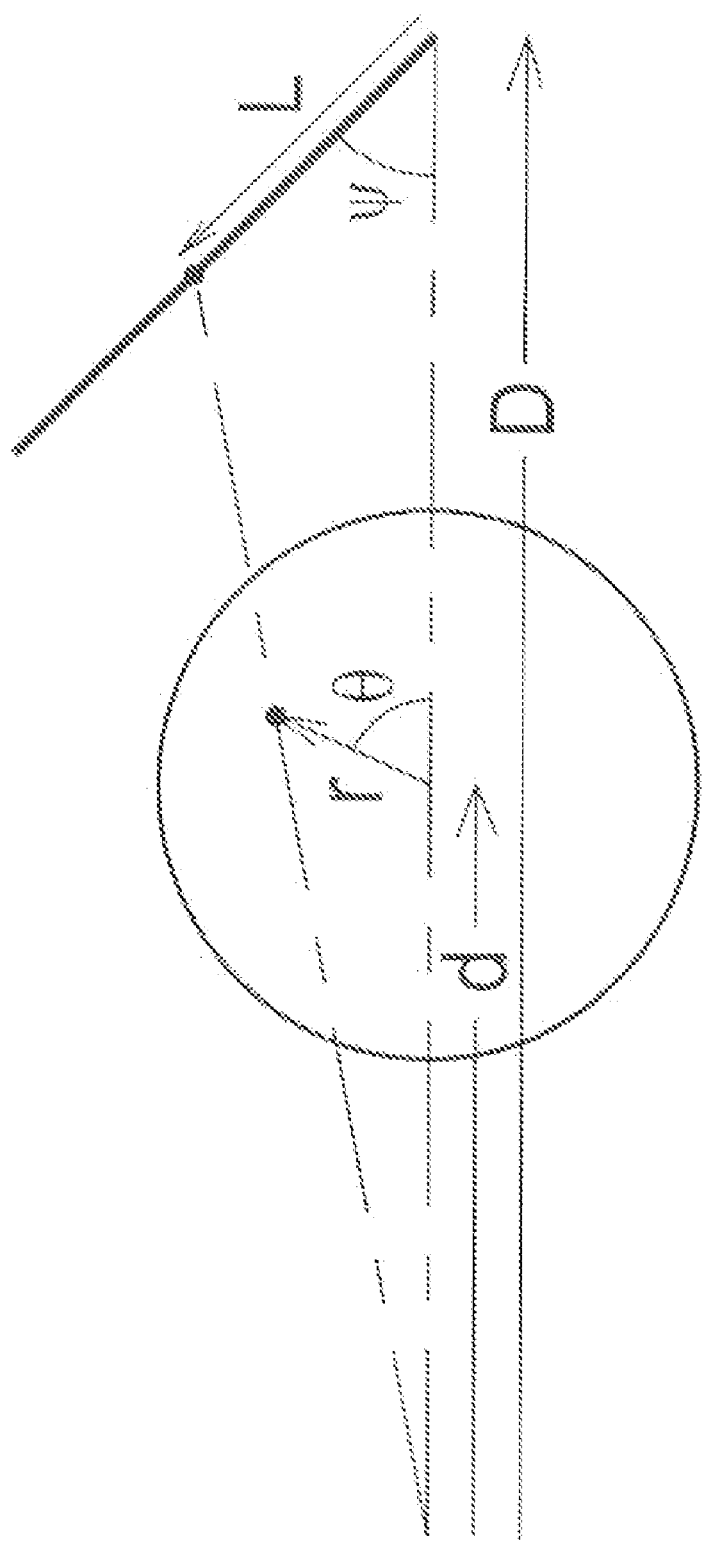
FIG. 3 depicts the mapping of an object point to VRX space according to a preferred embodiment of the invention.

Prior to scanning a subject 16 and constructing images, a calibration procedure is performed to specify the geometry of the four detector arms 20a-20b and 22a-22b. In a preferred embodiment of the invention, the calibration procedure involves moving an x-ray "shadow" of a metal pin across the entire detector array during a scan and mapping the position of the shadow. This may be accomplished by mounting the pin on a rotating platform in the scan field 32, with the pin positioned far enough away from the platform's center of rotation so that the pin's shadow will pass across the entire detector array during a rotation of the platform. A calibration algorithm executed on the computer system 28 determines twelve geometrical parameters (three for each arm of the array). These parameters include the angular rotation and translation in two directions of each arm in the scan plane. The calibration mapping equation is expressed as:

$$L = \frac{rD\sin\theta}{r\sin(\theta - \psi) - d\sin\psi},$$

where L, r, D, d, $\theta$ and $\psi$ are depicted in FIG. 3.

Figure 4:
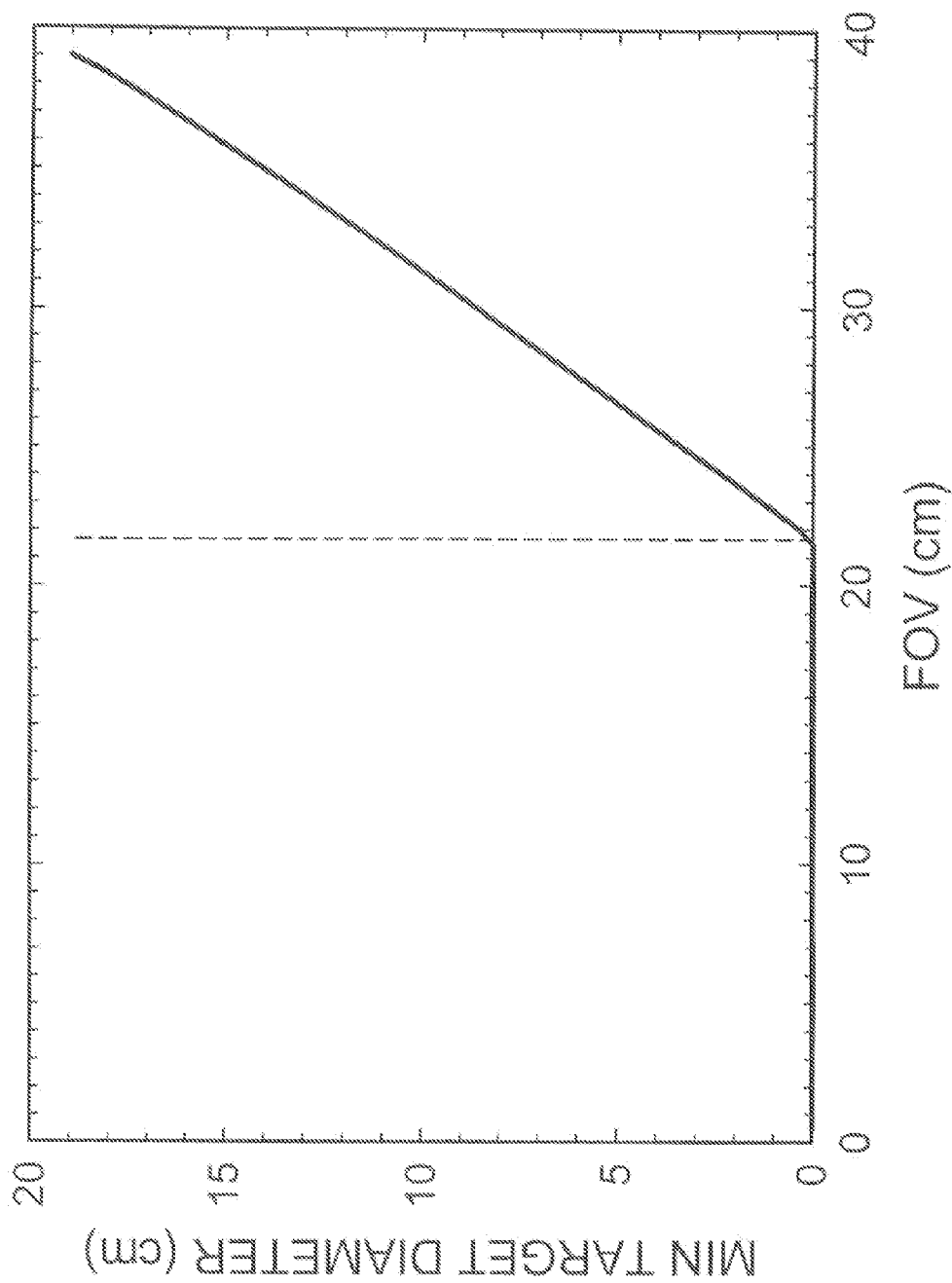
FIG. 4 depicts minimum target field diameter vs. outer field of view (FOV) according to a preferred embodiment of the invention.

If it is assumed for simplicity that each detector cell 24 yields a rectangular aperture response whose width equals the projected cell spacing, the minimum target field and maximum target resolution may be determined. For an embodiment of the system 10 having a spacing of 150 cm between the source 12 and the array vertex where the inner arms 22a-22b meet, a spacing of 102 cm between the source 12 to the center of the zone 32, and a detector arm length of 14.4 cm, the minimum target diameter is shown in FIG. 4 and the maximum cut-off frequency is shown in FIG. 5.

Figure 5:
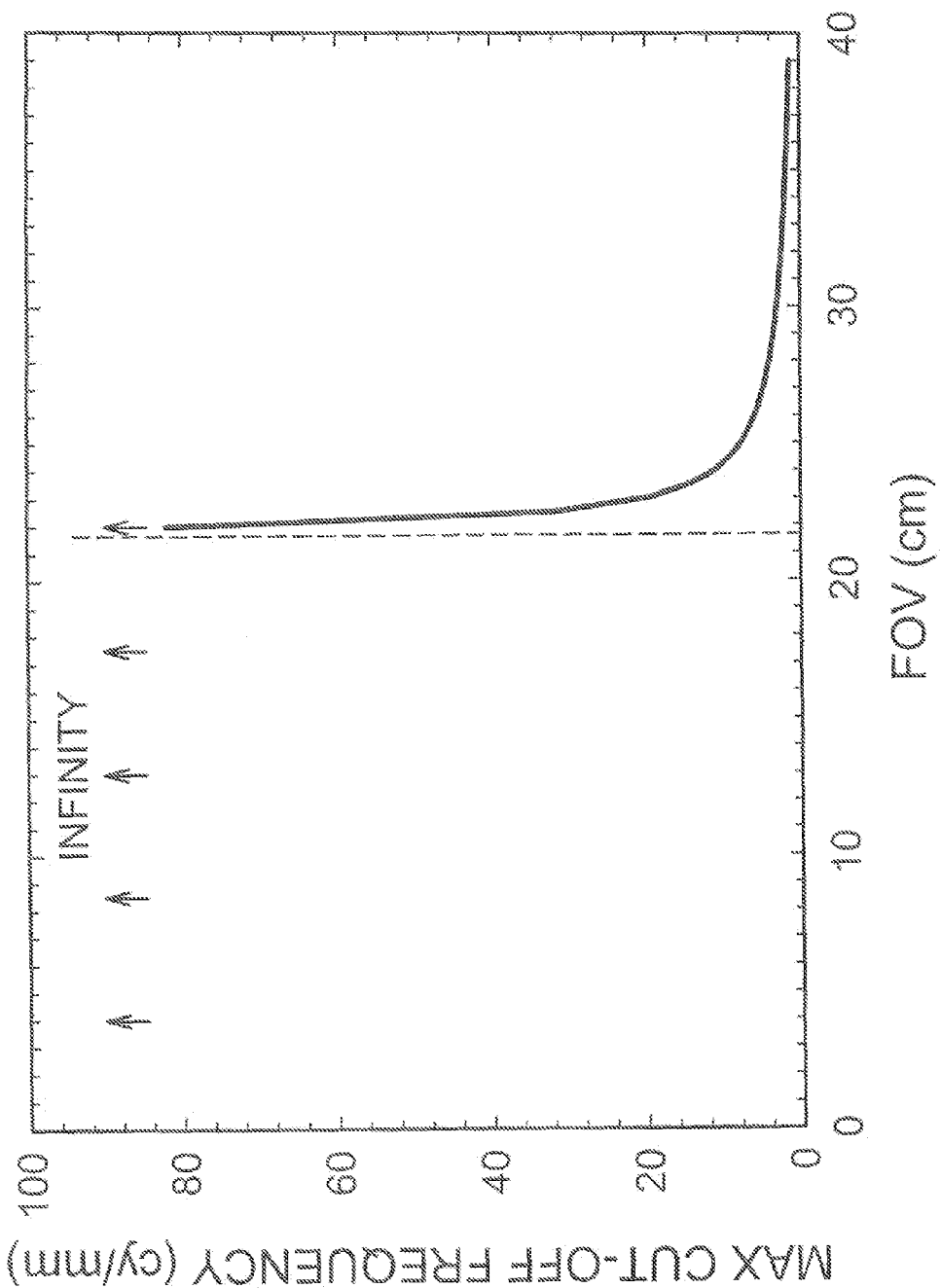
FIG. 5 depicts maximum cut-off frequency vs. outer FOV according to a preferred embodiment of the invention.

The resolution specified in FIG. 5 refers to the center cell in the target detector array. These plots indicate only the minimum possible target field and the maximum possible target detector resolution for one embodiment for the geometrical parameters chosen. In an optimal targeting VRX CT scanner, the inner arms 22a-22b of the array 18 could be closed almost completely ($\psi_{1a} + \psi_{1b} \rightarrow$ zero), such that the maximum geometrical resolution approaches infinity. However, in practice there are limitations imposed on system resolution by the x-ray focal spot size, system magnification, minimum detectable signal, x-ray penetration and scatter in the detector (non-rectangular line spread function) and other factors.

Figure 6B:
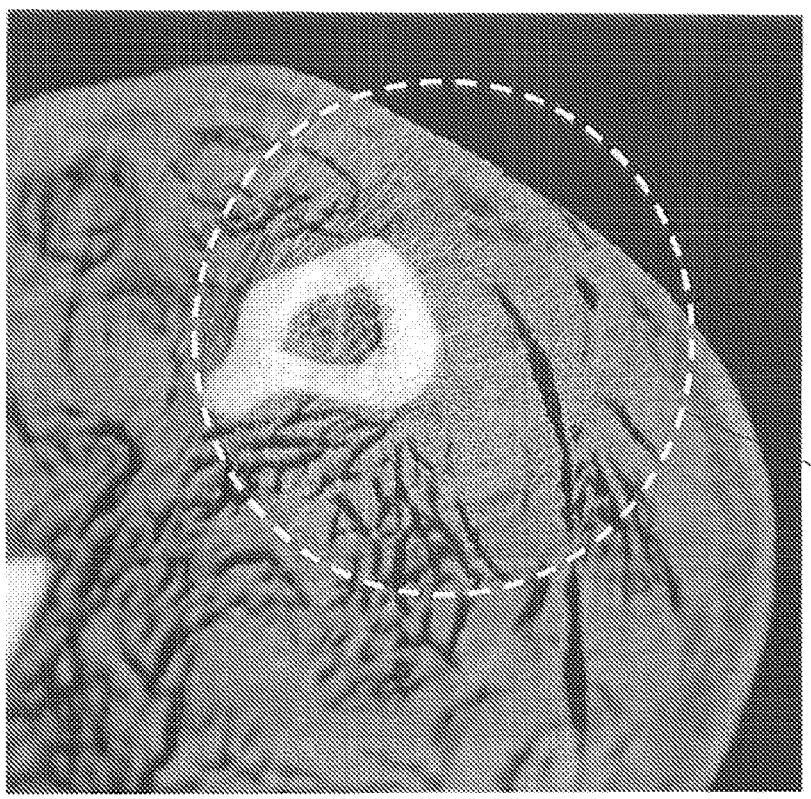
FIGS. 6A and 6B depict high-resolution VRX CT reconstructions of a section of a plasticized human forearm.
Figure 6A:
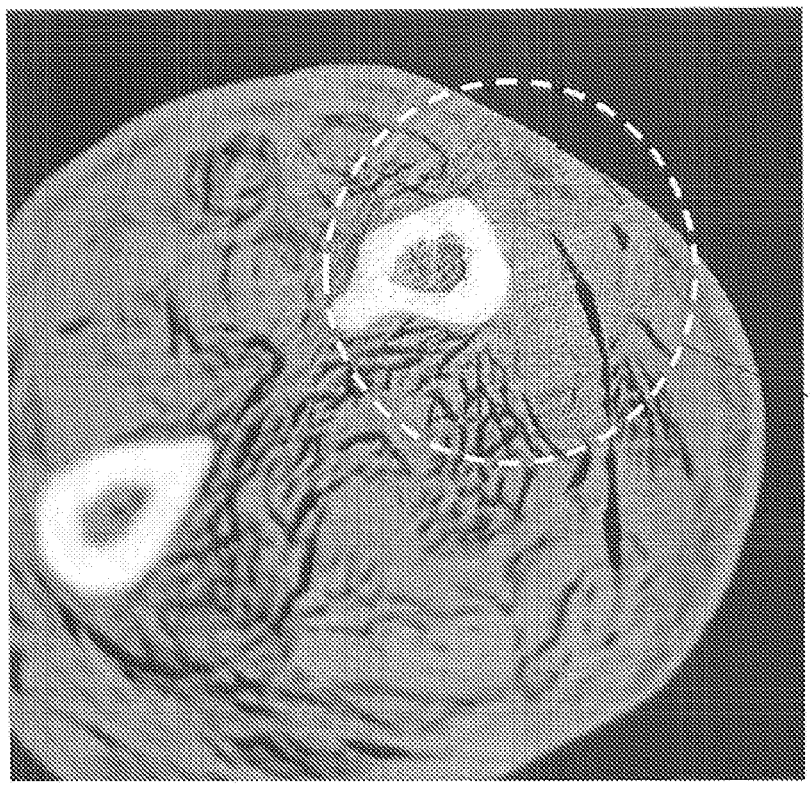

FIGS. 6A and 6B depict reconstructed images of a section of a plasticized human forearm made using an embodiment of the invention as depicted in FIG. 1. The target zone 30 is indicated by the dashed circle. Several features of these images are noteworthy: (1) the resolution of the target zone 30 is higher than in the rest of the image, which is apparent from the sharpness and structure present in the lower bone compared with the upper bone and from the sharpness of the micro-cracks or dark lines in the target zone: (2) there is no visible image artifact demarcating the transition from the target zone 30 to the outer zone; and (3) the target imaging has produced no discernable image artifacts.

Figure 7:
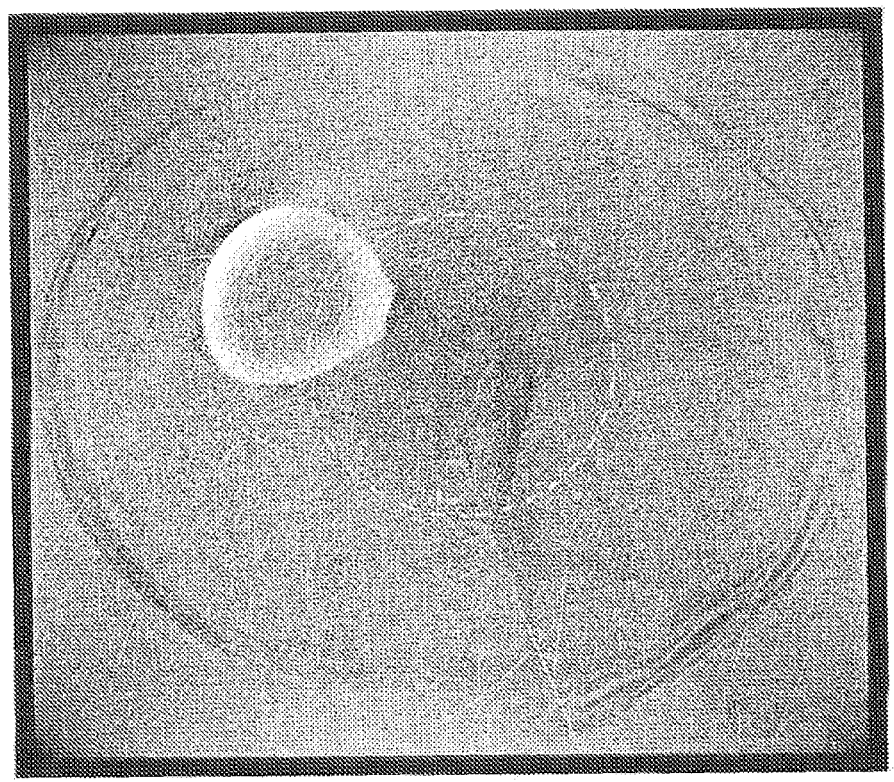
FIG. 7 depicts a high-resolution VRX CT reconstruction of a human thigh.

To determine the feasibility of high-resolution target imaging, a simulation was conducted based on experimental data. One purpose of the simulation was to determine whether significant resolution improvement could be obtained in the target zone 30 without introducing significant image artifacts. In conducting the simulation, a first scan was made of an anatomical specimen of a human thigh preserved in formalin using a single-arm storage phosphor CT scanner. An image reconstruction from this first scan is shown in FIG. 7. Anatomical features of note are the femur, calcified femoral artery, muscles outlined by fat, and subdermal straia. Soft tissue differentiation is inherently poor in the specimen because the formalin-perfused tissues are nearly isodense. (The "scratches" in the image are caused by imperfections in the storage phosphor screen.) The projection data comprise a sinogram having dimensions of 1400 samples by 1350 views with a sampling distance of 140 μm. The data were expanded (interpolated) to 2800 samples (70 µm sampling distance) to avoid loss of resolution in transforming from the spatially-linear high-resolution space to the equiangular space used in the reconstruction algorithm. The central section of FIG. 7 (within the dashed circle) depicts the high-resolution CT target data. For purposes of this simulation, it is important that high-contrast structure be present outside the target field to properly test for the production or absence of artifacts.

Figure 8:
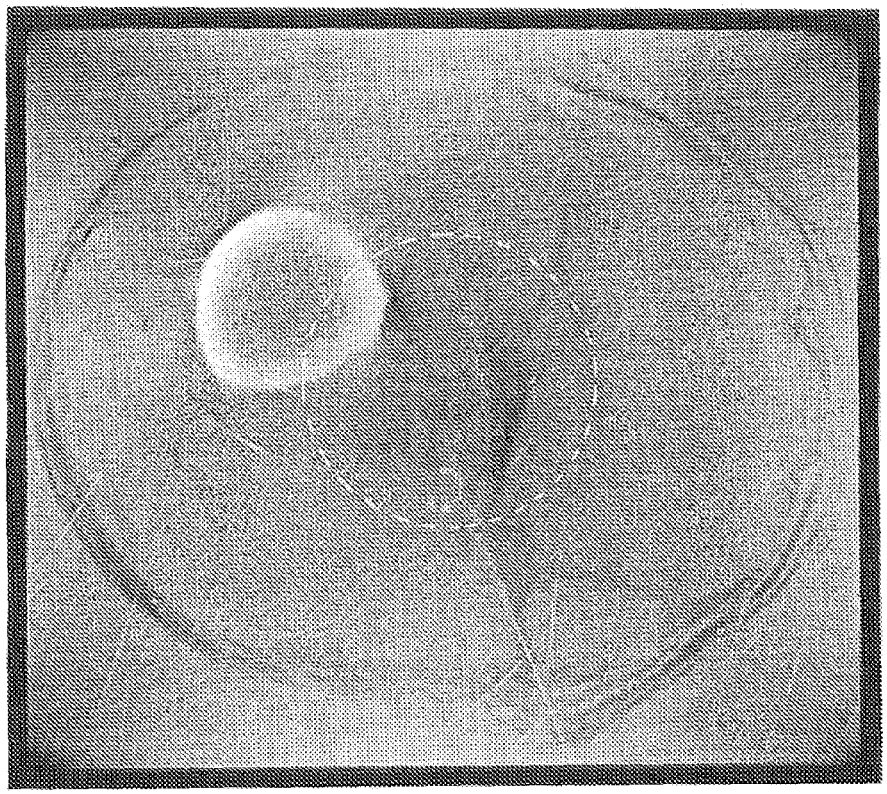
FIG. 8 depicts a low-resolution VRX CT reconstruction of a human thigh.

The low-resolution full-field data were then simulated by averaging the expanded fill projection data set over groups of two adjacent pre-expansion samples down to 700 samples (280 µm). This corresponds to the image shown in FIG. 8. The low-resolution data were obtained from the high-resolution data by averaging rather than by rescanning, to avoid problems with the geometrical fidelity (non-flatness) of the tilted storage phosphor screen and with image registration. Comparing the original high-resolution sampling with the low-resolution sampling, the spatial resolution in FIG. 8 should be approximately one-half that in FIG. 7.

Figure 9:
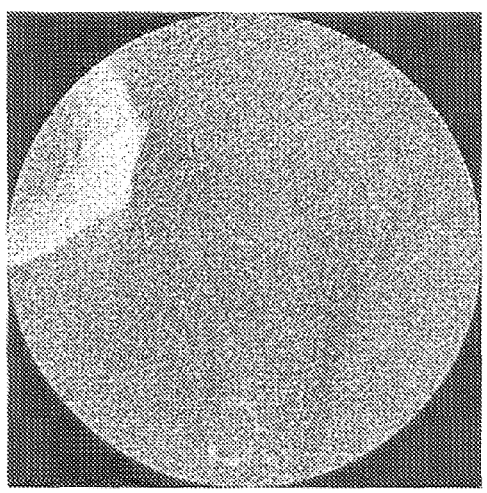
FIG. 9 depicts reconstructions of a VRX CT scan in the target zone made with an original high-resolution data set (left), a target data set (center) and a low-resolution data set (right)
Figure 9:
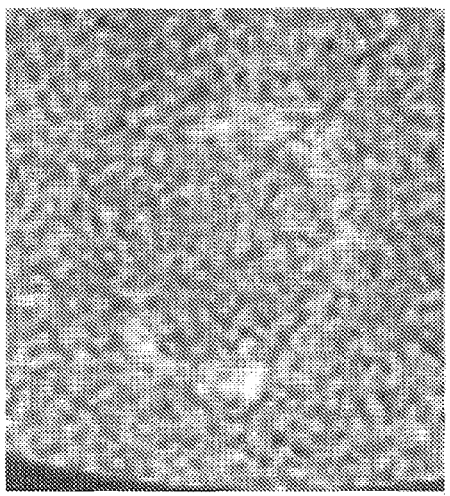
Figure 9:
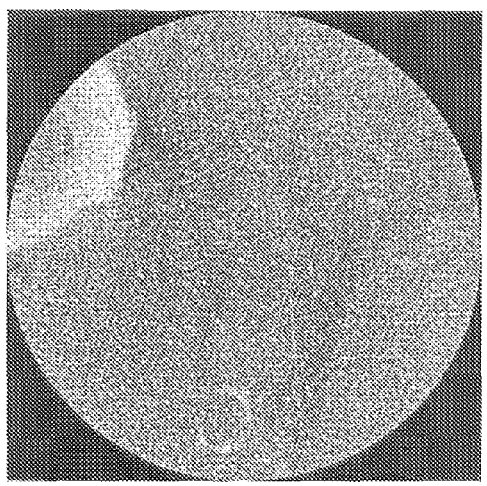
Figure 9:
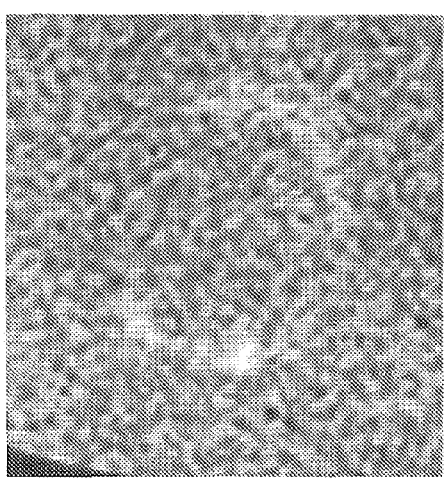
Figure 9:
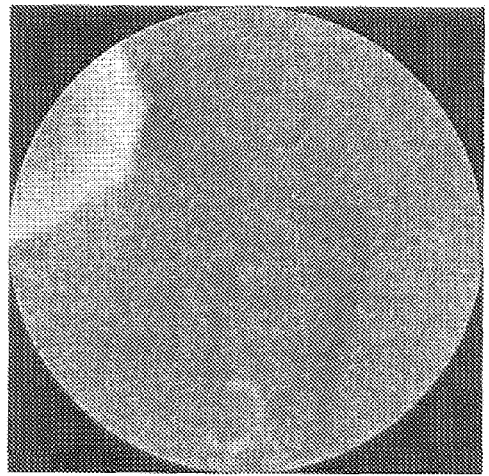
Figure 9:
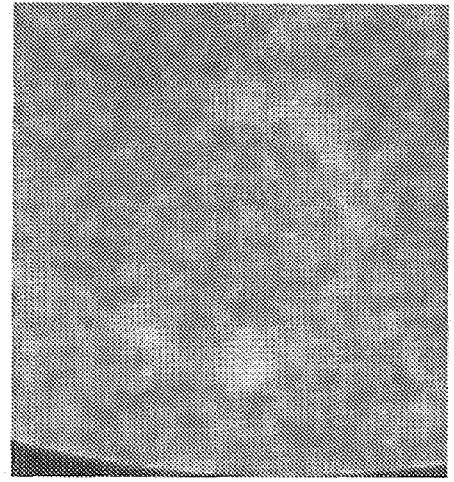

The target reconstruction was made by discarding the high-resolution data outside the target region and using the low-resolution data to fill in the sinogram outside the high-resolution target region. FIG. 9 compares target zones of (a) the high-resolution reconstruction, (b) the target reconstruction and (c) the low-resolution reconstruction. This simulation indicates that the target reconstruction preserves most of the high resolution of the original image. The general image quality and absence of artifacts in the target reconstruction are noteworthy.

In principle, embodiments of the system 10 could be used only in a targeting mode, such as depicted in FIG. 1. However, it is probably more feasible to first scan a subject in a non-targeting mode, where each inner arm 22a-b is aligned in parallel with its adjacent outer arm 20a-b so as to simulate a two-arm configuration ($\psi_{1a}=\psi_{2a}$, $\psi_{1b}=\psi_{2b}$). This first scan could be done at the lowest possible x-ray dose that still reveals the morphology upon which the target region will be chosen. Then, a technician could observe the reconstructed image from the first scan and identify the target region-of-interest on a display screen of the computer system 28, such as by using a screen cursor. Once the target region is identified, the subject 16 can be automatically moved laterally so that the target region is centered in the target zone 30. Then the system 10 can be adjusted to the high-resolution configuration (FIG. 1) and the target scan performed.

Another possibility is not to reposition the subject 16, but to have the inner arms 22a-b constantly sliding sideways during the scan so that they always remain directly behind the target zone. Advantages of this technique are that the patient does not have to be repositioned and there is reduced danger of the subject being pressed into the arms of the scanner array 18. The latter problem should be avoided anyway because the perimeter of the subject 16 is known from the first CT scan.

Figure 10:
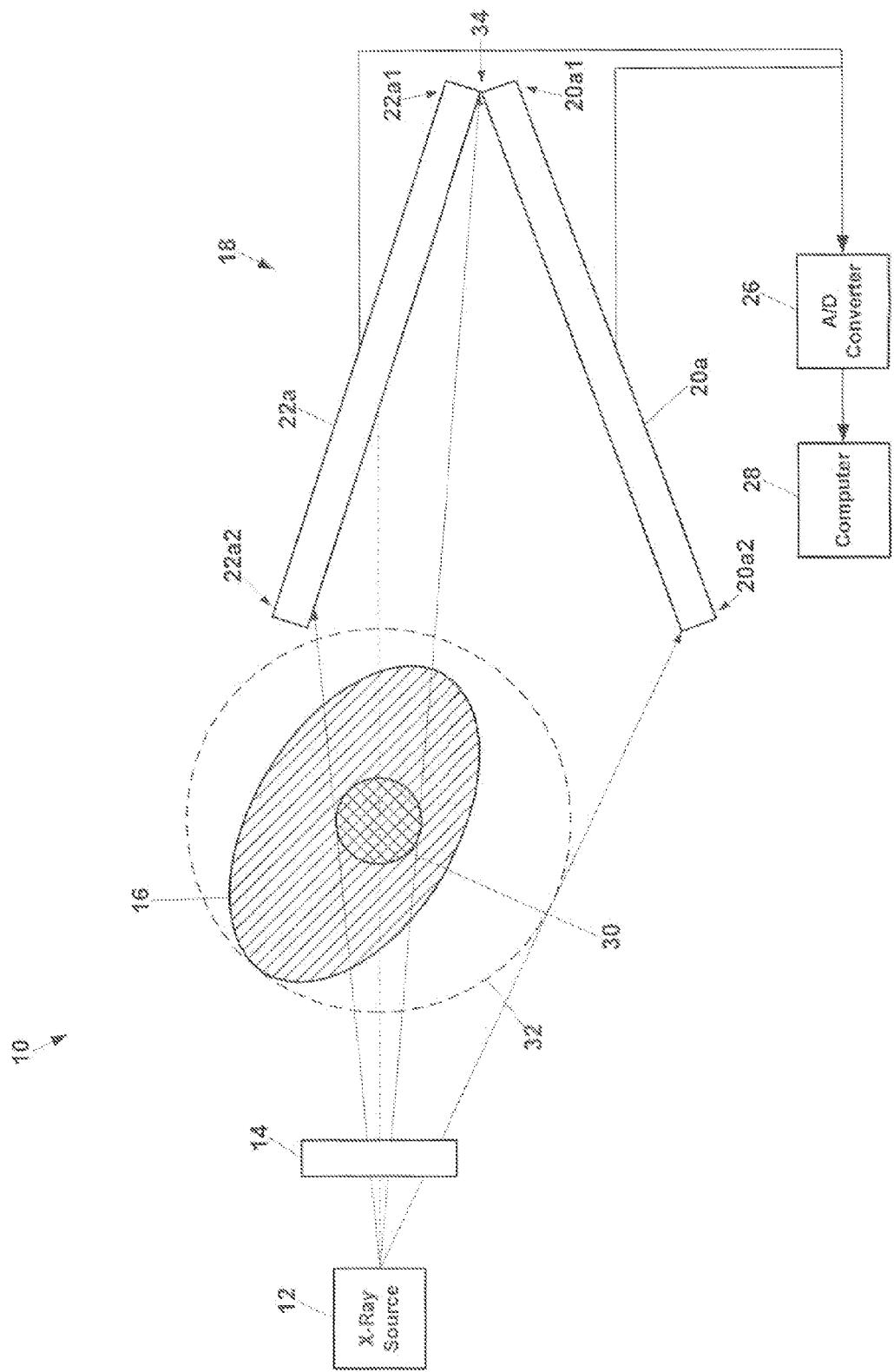
FIG. 10 depicts a dual-arm TVRX-CT scanner according to an alternative embodiment of the invention.
Figure 11:
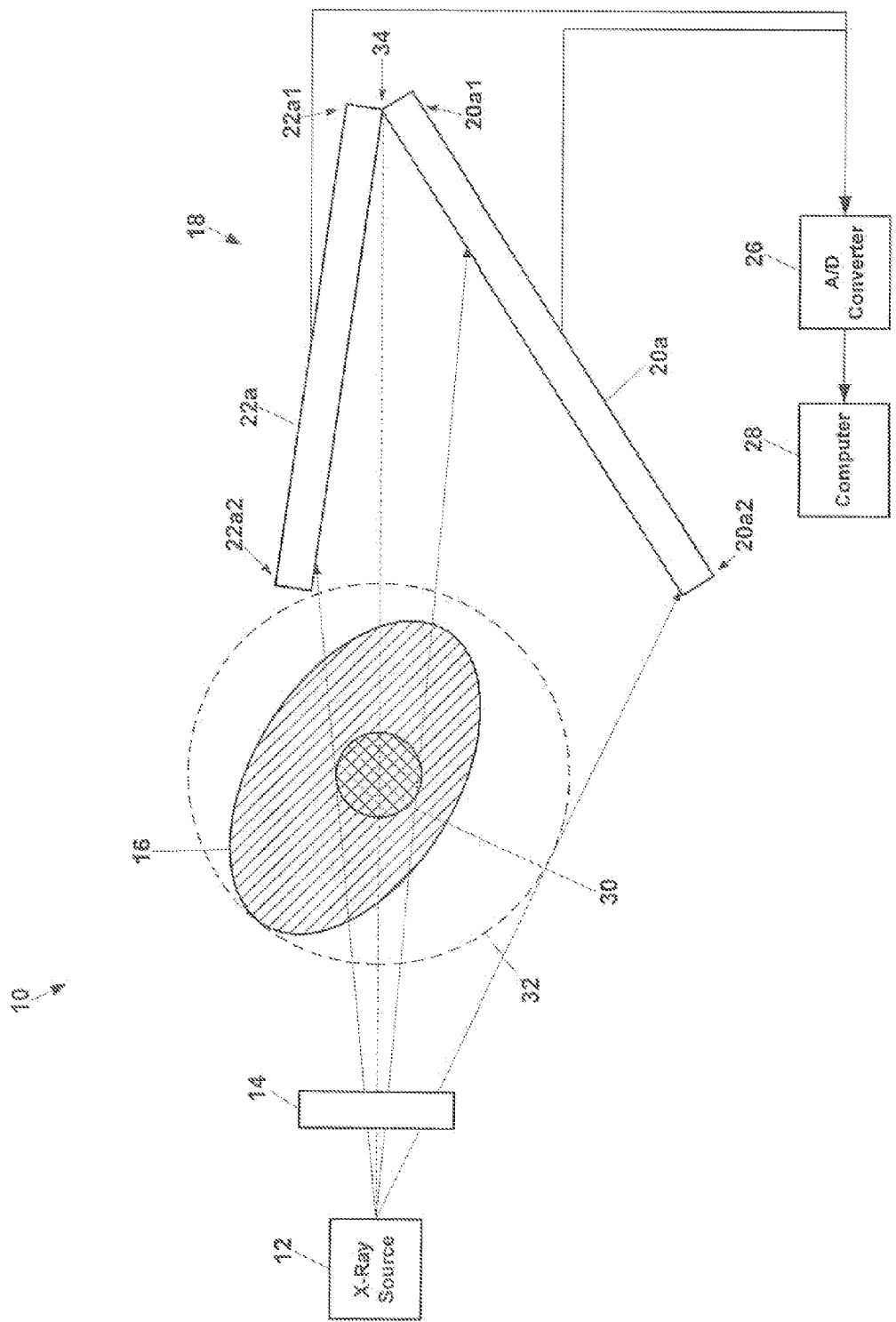
FIG. 11 depicts a dual-arm TVRX-CT scanner according to another alternative embodiment of the invention.

While preferred embodiments of the invention provide four arms (as shown in FIGS. 1 and 2), it is also possible to obtain high-resolution targeting functionality with a dual-arm VRX scanner by substantially increasing the angulation of one arm (the "target" arm), while the angulation of the other arm (the "outer" arm) remains substantially the same. This is shown in FIGS. 10 and 11. One disadvantage of this scheme as compared to four-arm embodiments is that the anatomy in the outer zone is sampled only once, not twice (from opposite directions) as is done in normal CT and VRX-CT scanning. This may create some shading artifacts in the outer zone, but not in the target zone. In the embodiment depicted in FIG. 10, the full double sampling requirement (at opposite directions) is met everywhere inside the target zone. Also, there is no central gap in this embodiment. However the target resolution is approximately two times lower than in the embodiment of FIG. 1. In the FIG. 11 embodiment, the entire situation is reversed. Hence, it appears that the preferred mode may depend on the particular application. In yet another embodiment, a third arm may be added to span the upper part of the outer field depicted in FIGS. 10 and 11.

As described herein, various embodiments of the invention can image subjects in a target imaging mode using a multi-arm VRX detector system, where the subject ranges in size from that of human patients to small animals and down to microscopy samples. Thus, the invention allows a focal anatomical region to be imaged at even higher resolution than has been previously possible using prior high-resolution CT techniques.

Although a preferred embodiment of the system 10 includes a detector array 18 having four arms, it will be appreciated that the invention is not limited by the number of arms provided in the array. For example, the embodiments depicted in FIGS. 10 and 11 include detector arrays having two arms. In other embodiments, the detector array may include three, five, or more arms positioned at various ψ angles to provide multiple zones having different resolution levels.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus for generating x-ray images of a subject, the apparatus comprising:

an x-ray radiation source for directing x-ray radiation along a radiation axis toward the subject; and a detector array for receiving the x-ray radiation as altered by the subject, the detector array comprising a plurality of array arms, each array arm including a plurality of detector cells for receiving and detecting the x-ray radiation at a spatial resolution which is dependent at least in part on the number of detector cells in each array arm and the orientation of the array arms with respect to the radiation axis of the x-ray radiation source, the plurality of array arms including:

a first array arm operable to be positioned at a first angle with respect to the radiation axis, the first array arm having a first spatial resolution determined at least in part by a value of the first angle, the first array arm including a first portion of the detector cells for receiving and detecting x-ray radiation that passes through a first zone of the subject; and a second array arm operable to be positioned at a second angle with respect to the radiation axis, the second array arm having a second spatial resolution determined at least in part by a value of the second angle which may be different from the value of the first angle, the second array arm including a second portion of the detector cells for receiving and detecting x-ray radiation that passes through a second zone of the subject;

a third array arm operable to be positioned at a third angle with respect to the radiation axis, the third array arm having a third spatial resolution determined at least in part by a value of the third angle, the third array arm including a third portion of the detector cells for receiving and detecting x-ray radiation that passes through the first zone of the subject; and a fourth array arm operable to be positioned at a fourth angle with respect to the radiation axis, the fourth array arm having a fourth spatial resolution determined at least in part by a value of the fourth angle which may be different from the value of the third angle, the fourth array arm including a fourth portion of the detector cells for receiving and detecting x-ray radiation that passes through the second zone of the subject; and means for processing signals generated by the detector cells of the detector array to generate a human-perceivable image of the subject.

2. The apparatus of claim 1 wherein the radiation axis of the x-ray radiation source coincides with an X-axis of an XYZ coordinate system, and the first and second angles are defined in an X-Y plane of the XYZ coordinate system.

3. The apparatus of claim 2 further comprising means for rotating the subject about a Z-axis of the XYZ coordinate system.

4. The apparatus of claim 2 further comprising means for moving the detector array and x-ray radiation source about a Z-axis of the XYZ coordinate system, where the subject is disposed on or adjacent the Z-axis.

5. The apparatus of claim 1 further comprising a slice collimator for directing at least a portion of the x-ray radiation to a specific slice of the subject.

6. The apparatus of claim 1 wherein:
the first array arm includes a first end and a second end, and the first array arm is operable to pivot about its first end; and
the second array arm includes a first end and a second end, and the second array arm is operable to pivot about its first end,
wherein the first end of the second array arm is disposed adjacent the second end of the first array arm.

7. The apparatus of claim 6 wherein the first angle has a value ranging from about zero degrees to about ninety degrees, and the second angle has a value ranging from about the value of the first angle to about ninety degrees.

8. The apparatus of claim 1 wherein the value of the first angle is substantially equivalent to the value of the third angle, and the value of the second angle is substantially equivalent to the value of the fourth angle.

9. The apparatus of claim 1 wherein:
the third array arm includes a first end and a second end, and the third array arm is operable to pivot about its first end; and
the fourth array arm includes a first end and a second end, and the fourth array arm is operable to pivot about its first end,
wherein the first end of the fourth array arm is disposed adjacent the second end of the third array arm.

10. The apparatus of claim 9 wherein the third angle has a value ranging from about zero degrees to about ninety degrees, and the fourth angle has a value ranging from about the value of the third angle to about ninety degrees.

11. The apparatus of claim 9 wherein:
the first array arm includes a first end and a second end, and the first array arm is operable to pivot about its first end; and
the second array arm includes a first end and a second end, and the second array arm is operable to pivot about its first end,
wherein the first end of the second array arm is disposed adjacent the second end of the first array arm, and the first end of the first array arm is disposed adjacent the first end of the third array arm.

12. The apparatus of claim 11 wherein the first and second array arms are disposed to one side of the radiation axis and the third and fourth array arms are disposed to an opposite side of the radiation axis.

13. The apparatus of claim 11 wherein the first end of the first array arm and the first end of the third array arm form a vertex of the detector array which is disposed on or adjacent the radiation axis.

14. The apparatus of claim 1 wherein the detector cells comprise $CdWO_4$ crystal-photodiode scintillator cells.

15. The apparatus of claim 1 wherein the value of the first angle is smaller than the value of the second angle so that the first spatial resolution is greater than the second spatial resolution, resulting in the human-perceivable image having an image resolution which is greater for the first zone of the subject than for the second zone of the subject.

16. The apparatus of claim 1 wherein:
the first array arm includes a first end and a second end, and the first array arm is operable to pivot about its first end; and
the second array arm includes a first end and a second end, and the second array arm is operable to pivot about its first end,
wherein the first end of the second array arm is disposed adjacent the first end of the first array arm.

17. An apparatus for generating x-ray images of a subject, the apparatus comprising:
an x-ray radiation source for directing x-ray radiation along a radiation axis toward the subject; and
a detector array for receiving the x-ray radiation as altered by the subject, the detector array comprising a plurality of array arms, each array arm including a plurality of detector cells for receiving and detecting the x-ray radiation at a spatial resolution which is dependent at least in part on the number of detector cells in each array arm and the orientation of the array arms with respect to the radiation axis of the x-ray radiation source, the plurality of array arms including:
a first array arm operable to be positioned at a first angle with respect to the radiation axis, the first angle having a value ranging from about zero degrees to about ninety degrees, the first array arm having a first spatial resolution determined at least in part by the value of the first angle, the first array arm including a first portion of the detector cells for receiving and detecting x-ray radiation that passes through a first zone of the subject, the first array arm including a first end and a second end, wherein the first array arm is operable to pivot about its first end;
a second array arm operable to be positioned at a second angle with respect to the radiation axis, the second angle having a value ranging from about the value of the first angle to about ninety degrees, the second array arm having a second spatial resolution determined at least in part by the value of the second angle, the second array arm including a second portion of the detector cells for receiving and detecting x-ray radiation that passes through a second zone of the subject, the second array arm including a first end and a second end, wherein the second array arm is operable to pivot about its first end, and wherein the first end of the second array arm is disposed adjacent the second end of the first array arm;

a third array arm operable to be positioned at a third angle with respect to the radiation axis, the third angle having a value that is substantially equivalent to the value of the first angle, the third array arm having a third spatial resolution determined at least in part by the value of the third angle, the third array arm including a third portion of the detector cells for receiving and detecting x-ray radiation that passes through the first zone of the subject, the third array arm including a first end and a second end, wherein the third array arm is operable to pivot about its first end; and a fourth array arm operable to be positioned at a fourth angle with respect to the radiation axis, the fourth angle having a value that is substantially equivalent to the value of the second angle, the fourth array arm having a fourth spatial resolution determined at least in part by the value of the fourth angle, the fourth array arm including a fourth portion of the detector cells for receiving and detecting x-ray radiation that passes through the second zone of the subject, the fourth array arm including a first end and a second end, wherein the fourth array arm is operable to pivot about its first end, and wherein the first end of the fourth array arm is disposed adjacent the second end of the third array arm, wherein the first and second array arms are disposed to one side of the radiation axis and the third and fourth array arms are disposed to an opposite side of the radiation axis, wherein the first end of the first array arm and the first end of the third array arm form a vertex of the detector array which is disposed on or adjacent the radiation axis; and means for processing signals generated by the detector cells of the detector array to generate a human-perceivable image of the subject.

18. An apparatus for generating x-ray images of a subject, the apparatus comprising:

an x-ray radiation source for directing x-ray radiation along a radiation axis toward the subject; and a detector array for receiving the x-ray radiation as altered by the subject, the detector array comprising a plurality of array arms, each array arm including a plurality of detector cells for receiving and detecting the x-ray radiation at a spatial resolution which is dependent at least in part on the number of detector cells in each array arm and the orientation of the array arms with respect to the radiation axis of the x-ray radiation source, the plurality of array arms including:

a first array arm operable to be positioned at a first angle with respect to the radiation axis, the first array arm having a first spatial resolution determined at least in part by a value of the first angle, the first array arm including a first portion of the detector cells for receiving and detecting x-ray radiation that passes through a first zone of the subject; and a second array arm operable to be positioned at a second angle with respect to the radiation axis, the second array arm having a second spatial resolution determined at least in part by a value of the second angle which may be different from the value of the first angle, the second array arm including a second portion of the detector cells for receiving and detecting x-ray radiation that passes through a second zone of the subject, wherein the first end of the first array arm is disposed adjacent the first end of the second array arm, whereby the first and second array arms form a vertex of the detector array, wherein the first angle and the second angle are both acute angles, and the value of the first angle is smaller than the value of the second angle so that the first spatial resolution is greater than the second spatial resolution, resulting in an image resolution which is greater for the first zone of the subject than for the second zone of the subject; and means for processing signals generated by the detector cells of the detector array to generate a human-perceivable image of the subject.

19. The apparatus of claim 18 wherein the vertex of the detector array is disposed on or adjacent the radiation axis.

* * * * *